United States Patent [19]
Helling et al.

[11] Patent Number: 5,229,520
[45] Date of Patent: Jul. 20, 1993

[54] POLYCHLORODIPYRIDOIMIDAZOLIUM COMPOUNDS AND THEIR USE IN THE PREPARATION OF PENTACHLOROPYRIDINE

[75] Inventors: Richard K. Helling, Martinez, Calif.; Kent P. Steele, Indianapolis, Ind.; Terrill E. Applebury, Lafayette, Calif.

[73] Assignee: DowElanco, Indianapolis, Ind.

[21] Appl. No.: 780,189

[22] Filed: Oct. 22, 1991

[51] Int. Cl.$^5$ ............... C07D 213/26; C07D 213/127
[52] U.S. Cl. ........................ 546/345; 546/85; 546/2
[58] Field of Search ................. 546/345, 346

[56] References Cited

U.S. PATENT DOCUMENTS

| | | | |
|---|---|---|---|
| 3,186,994 | 6/1965 | Johnston et al. | 546/345 |
| 4,227,001 | 10/1980 | Dietsche et al. | 546/345 |
| 4,256,894 | 3/1981 | Dietsche et al. | 546/345 |
| 4,517,369 | 5/1985 | Marinak et al. | 546/345 |
| 4,681,945 | 7/1987 | Humphreys et al. | 546/345 |
| 4,723,019 | 2/1988 | Okorley et al. | 546/345 |

OTHER PUBLICATIONS

Suschitzky, *Polychloroaromatic Compounds*, Plenum Press, 225–231 (1974).
Hamana et al., *Chemical and Pharmaceutical Bulletin*, 11, 694–699 (1963).
Bradsher et al., *J. Org. Chem.*, 35, 2495–2497 (1970).
Pauls et al., *Chem. Ber.*, 109, 3646–3652 (1976).
Edward et al., *J. Org. Chem.* 50, 4855–4861 (1985).
Jones et al., *J. Chem. Soc. Perkin Trans.*, 1, 2585–2592 (1987).
Brown et al., *J. Chem. Soc.*, 2040–2042 (1959).

*Primary Examiner*—Alan L. Rotman
*Attorney, Agent, or Firm*—D. Wendell Osborne

[57] ABSTRACT

Polychlorodipyridoimidazolium tetrachloroferrate compounds, such as 1,2,3,4,11-pentachloro-8-(trichloromethyl)dipyrido[1,2-a:1',2'-]imidazol-10-ium tetrachloroferrate, which are obtained as by-products in the preparation of polychloropyridine and polychloropicoline compounds by chlorination of many chloro(trichloromethyl)pyridine compounds in the presence of ferric chloride catalyst and can be prepared by heating a mixture of a chloro-2-(trichloromethyl)-pyridine compound with a 2-chloro-5-(trichloromethyl)pyridine compound, can be converted to pentachloropyridine by chlorination at temperatures above about 230° C. and pressures above about 300 psig (2.17 mPa).

6 Claims, No Drawings

POLYCHLORODIPYRIDOIMIDAZOLIUM COMPOUNDS AND THEIR USE IN THE PREPARATION OF PENTACHLOROPYRIDINE

BACKGROUND OF THE INVENTION

This invention relates to the preparation of pentachloropyridine by the chlorination of compounds containing a pyridine ring nucleus and to compounds of this type.

Pentachloropyridine is a well-known chemical intermediate with many industrial applications. It is generally prepared by the chlorination of pyridine, picolines or lutidines or of partially chlorinated pyridine, picoline or lutidine compounds at relatively high temperatures, sometimes in the presence of Lewis acid catalysts. Many such methods are summarized in the book, *Polychloroaromatic Compounds* by Suschitzki, Plenum Press, 1974, pages 225-231. The discovery of methods of preparing pentachloropyridine by simple processes from cheap and available starting materials, however, is of continuing interest.

SUMMARY OF THE INVENTION

It has now been found that pentachloropyridine can be prepared by the chlorination of polychlorodipyridoimidazolium tetrachloroferrate compounds in the liquid phase at elevated temperatures and pressures and, optionally, in the presence of a Lewis acid catalyst, such as ferric chloride.

The invention includes a process for preparing pentachloropyridine which comprises chlorinating a polychlorodipyridoimidazolium tetrachloroferrate compound of Formula I

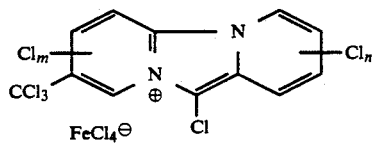

Formula I wherein
m represents the number 0 or 1: and
n represents the number 1, 2, 3, or 4
at a temperature of at least about 230° C. and a pressure of at least about 200 psig (1.48 mPa (megaPascals)), optionally in the presence of a Lewis acid catalyst.

Mixtures of compounds containing one or more polychlorodipyridoimidazolium compounds of Formula I, such as those mixtures obtained as non-volatile by-products in the preparation of chlorinated pyridines and picolines by the chlorination of picolines are preferred starting materials.

Temperatures of about 230° C. to about 350° C. and pressures of about 300 psig (2.17 mPa) to about 1000 psig (7.00 mPa) are often preferred.

The novel compounds of Formula I are a further embodiment of the present invention.

DETAILED DESCRIPTION OF THE INVENTION

The polychlorodipyridoimidazolium compounds of Formula I that are chlorinated to produce pentachloropyridine in the process of the present invention include those of Formula I wherein m represents the number 0 or 1 and n represents the number 1, 2, 3, or 4. Compounds wherein m represents 0 and n represents 3 or 4 are sometimes preferred. The compound of Formula IA, 1,2,3,4,11-pentachloro-8-(trichloromethyl)-dipyrido-[1,2-a:1′,2′-cimidazol-10-ium tetrachloroferrate,

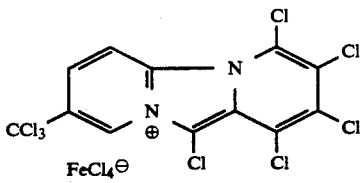

Formula IA is illustrative. The compounds of Formula I are typically employed in the process as a mixture containing at least one such compound along with other chlorinated materials, which serve as diluents.

The process is preferably carried out by adding chlorine to a mixture of a compound of Formula I and a liquid diluent at a temperature above about 230° C. and a pressure above about 300 psig (2.17 mPa). Temperatures below about 350° C. and pressures below about 1000 psig (7.00 mPa) are usually employed. Temperatures of about 250° C. and pressures of about 350 psig (2.52 mPa) are often preferred. A Lewis acid catalyst, if employed, is typically used in amounts of about 1 to about 20 percent of the mixture being chlorinated. Chlorine is typically employed in an amount in excess of the stoichiometric amount. The mixture is typically agitated during the chlorination reaction.

Suitable diluents for the process include chlorinated pyridine and picoline compounds that are liquid at temperatures above 230° C. These compounds, except for pentachloropyridine, are typically also susceptible to chlorination under the process conditions and are generally converted to higher chlorinated pyridines and picolines. Typically, the diluent is a mixture of chlorinated pyridine and picoline compounds. Pentachloropyridine is often a preferred diluent.

Lewis acid catalysts are often helpful in the process. Metal chloride Lewis acid catalysts, such as ferric chloride, zinc chloride, nickel chloride, and aluminum chloride are preferred. Ferric chloride is especially preferred. It is often convenient to employ a precursor to a suitable metal chloride, such as a metal, for example, iron or zinc, or a metal oxide, for example, aluminum oxide, instead of a metal chloride. Such compounds are converted to suitable metal chlorides under the reaction conditions. Any amount of an effective Lewis acid catalyst may be employed and will be useful. Amounts up to about 20 percent of the reaction mixture are suitable and amounts of from about 1 percent to about 10 percent of the reaction mixture are more typical.

The chlorination is continued until it is substantially complete, which can be ascertained by observing the disappearance or substantial reduction in concentration of the compound of Formula I. The pentachloropyridine produced can be and typically is recovered by distillation of the chlorination mixture. It can also be recovered by extraction with an organic solvent or super-critical carbon dioxide. Good yields of high purity pentachloropyridine can be obtained.

The starting materials of Formula I can be prepared by the reaction of a 2-(trichloromethyl)-pyridine compound of Formula II

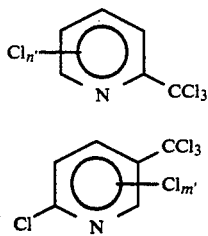

FORMULA II

FORMULA III wherein n' represents the number 1, 2, 3, or 4 with a 3-trichloromethyl-2-chloropyridine compound of Formula III wherein m' represents the number 0 or 1 at elevated temperatures and in the presence of ferric chloride. The process is typically carried out by combining approximately equimolar quantities of two suitable (trichloromethyl)pyridine compounds, one of each of Formulas II and III, and of ferric chloride and heating the mixture at a temperature of about 180° C. to about 225° C. for about 1 to about 8 hours. The compound of Formula I prepared generally precipitates as a solid. It can usually be recovered by conventional means, such as decantation, centrifugation, and filtration, and can be purified by conventional means, such as by recrystallization from solvents or by liquid-liquid chromatography. Recrystallization from a mixture of a ketone solvent and a hydrocarbon solvent, such as mixtures of acetone and hexane, is typical.

The starting material polychlorodipyridoimidazolium compounds of Formula I are often obtained as by-products in the chlorination of mixtures of chloro-2-(trichloromethyl)pyridines and chloro-3-(trichloromethyl)pyridines. The chlorination of mixtures containing 2-chloro-6-(trichloromethyl)-pyridine, 2,3-di-chloro-6-(trichloromethyl)pyridine, 3,4,5-trichloro-2-(trichloromethyl)pyridine or 2,3,4,5-tetrachloro-6-(trichloromethyl)pyridine along with 2,6-dichloro-3-(trichloromethyl)pyridine or 2-chloro-5-(trichloromethyl)-pyridine, is typical. Such chlorinations are generally carried out in the liquid phase at temperatures of about 160° C. to 200° C. in the presence of ferric chloride catalyst and are often employed for the preparation of chlorinated pyridine and (trichloromethyl)-pyridine compounds, such as 2,3,6-trichloropyridine, 2,3,5,6-tetrachloropyridine, pentachloropyridine, 3,6-dichloro-2-(trichloromethyl)pyridine, 2,3-dichloro-5-(trichloromethyl)pyridine, 2,3,4,5-tetrachloro-6-(trichloromethyl)pyridine, and the like.

Compounds of Formula I that are obtained in the above-described manner are usually employed in the process of the present invention as mixtures containing the other chlorinated pyridine and picoline by-products and other high boiling or non-volatile by-products of the method. Such mixtures, which are often referred to as by-product tars, are currently considered to be waste material that must be disposed of. Thus, a waste stream can be converted into a useful product, pentachloropyridine, by the process of the present invention.

The following examples are presented to illustrate the invention and should not be construed as limiting to its scope.

EXAMPLES

Example 1 — Recovery of Compound of Formula IA From Chloropyridine Tars

A sample of tar from the chlorination of a mixture of chloro-2-(trichloromethyl)pyridines and chloro-3-(trichloromethyl)pyridines to 2,3,5,6-tetrachloropyridine was slurried in methylene chloride and the insoluble portion was collected by filtration. The resulting solids were washed with methylene chloride and then recrystallized from a mixture of acetone and hexane. 1,2,3,4,11-Pentachloro-8-(trichloromethyl)-dipyrido[1,2'-c]imidazol-10-ium tetrachloroferrate (compound of Formula IA) was recovered as red-/orange crystals. The compound did not melt, but decomposed on heating. The uv spectrum of the compound in acetonitrile exhibited strong absorptions at 198, 250 (molar absorptivity=44,300 absorbance units/cm), and 366 nanometers. The mass spectrum with fast atom bombardment had an ion with an m/e of 455 containing 8 chlorine atoms. The presence of a $CCl_3$ group was confirmed by hydrolysis to a carboxylic acid. The structure was confirmed by single crystal X-ray crystallography.

Calculated for $Cl_2H_3Cl_{12}FeN_2$ %Cl, 64.8; % Fe, 8.50, Found:,. %Cl, 62.1; % Fe, 8.37.

Example 2 — Synthesis of Compound of Formula IA and Analogs

A mixture of 5.03 g (15 mmol) of 2,3,4,5-tetrachloro-6-(trichloromethyl)pyridine, 3.47 g (15 mmol) of 2-chloro-5-(trichloromethyl)pyridine, and 2.43 g (15 mmol) of ferric chloride was heated to about 194–198° C. with stirring. After about 1 hr of reaction about half of the starting chloropicolines had disappeared and after about 4 hrs the reaction appeared to be complete. After 6 hr the mixture was cooled, diluted with acetonitrile, and analyzed by liquid-liquid chromatography using a $C_{18}$ column and an uv detector at 280 nanometers and eluting with acetonitrile containing 0.1 percent sulfuric acid. The mixture was found to be about 66 area percent of the compound of Formula IA.

Analogous products, as determined by similar movement in liquid-liquid chromatography and a strong uv absorption at about 350 nanometers, were obtained when equimolar amounts of the following pairs of chloropicolines along with ferric chloride were heated to about 180° C. to 225° C. with stirring: 2,3,4-trichloro-6-(trichloromethyl)pyridine and 2-chloro-5-(trichloromethyl)pyridine, 3,4,5-trichloro-2-(trichloromethyl)-pyridine and 2-chloro-5-(trichloromethyl)pyridine, 2,3,5-trichloro-6-(trichloromethyl)pyridine and 2-chloro-5-(trichloromethyl)pyridine, 2,3-dichloro-6-(trichloromethyl)pyridine and 2-chloro-5-(trichloro methyl)pyridine, 2-chloro-6-(trichloromethyl)pyridine and 2-chloro-5-(trichloromethyl)pyridine, 2,3,4,5-tetrachloro-6-(trichloromethyl)pyridine and 2,4-dichloro-5-(trichloromethyl)pyridine.

Example 3 — Pentachloropyridine by Chlorination of Compound of Formula IA

A 1 L batch Monel™ Parr™ bomb reactor (Model 4520) equipped with Monel™ inlet and outlet tubes each with a trap to ensure the separation and return to the reactor of any liquids entrained in the gases, a Monel™ sample tube, a thermowell, a 1000 psig rupture disc, an air-motor-powered magnetic-drive stirrer having two pitched-blade turbines, and a 1500-Watt heater was employed Chlorine was fed to the reactor through the inlet tube from a thermostated 2 L Monel™ Parr™ pressure vessel (Model M-4622) chlorine reservoir maintained at a temperature that would produce a chlorine pressure at least 40 psig greater than the pressure in the reactor by means of recirculated water-ethylene glycol mixture flowing through a copper tube jacket surrounding the vessel. The amount of chlorine in the vessel was continuously determined by its weight. The chlorine flow was kept constant by regulating the pressure drop across a nickel capillary tube and was measured by a Validyne ™ DP-15-30 differential pressure transducer equipped with a 1.25 psi differential rated diaphragm. The outlet tube was connected to a scrubber containing a 10 percent aqueous sodium hydroxide solution to remove chlorine and acids from the exiting gases.

The scrubber was filled with 10 percent aqueous sodium hydroxide solution and the chlorine reservoir vessel was cooled to 5° C. and loaded with liquid chlorine from a chlorine cylinder. The reactor was loaded with 200 g of compound of Formula IA and 200 g of pentachloropyridine (51 percent compound of Formula IA by liquid-liquid chromatography using an internal standard and 44 percent pentachloropyridine by gas-liquid chromatography using an internal standard) and was sealed. The chlorine reservoir vessel was then heated to 115° C., the reactor vessel was heated to about 100° C., and the stirrer was activated. Sufficient chlorine from the reservoir vessel was transferred to the reactor vessel to achieve the desired pressure of 550 psig (3.9 mPa) and the reactor vessel was then heated to the desired chlorination temperature of 300° C. The desired temperature range was arrived at and the system was stabilized at that temperature and 550 psig (3.9 mPa) pressure after about 1 to 2 hrs. After 6.5 hours the mixture was found to contain 74 percent pentachloropyridine and no compound of Formula IA.

Example 4 — Pentachloropyridine by Chlorination of a Mixture of By-products From the Chlorination of Chlorinated 2- and 3-(Trichloromethyl)pyridines The equipment and procedure described in Example 1 were employed. A 1100 g sample of a mixture of by-products from the chlorination of chlorinated alpha- and beta-(trichloromethyl)pyridines was employed. Samples of the chlorination mixture were analyzed before being placed in the reactor, intermittently during the chlorination, and at the conclusion of the chlorination. Chloropyridines, including pentachloropyridine, were analyzed quantitatively by standardized gas-liquid chromatography. The compound of Formula IA was analyzed quantitatively by standardized liquid chromatography. Positive identification of other volatile components was made by gas chromatography/mass spectroscopy. Metals were analyzed quantitatively by X-ray fluorescence fundamental parameters or by inductively coupled plasma atomic emission spectrometry. The reaction conditions are summarized in Table 1 and the results are summarized in Table 2.

TABLE 1

| Run No. | Temp., °C. | Chlorination Conditions | | | |
|---|---|---|---|---|---|
| | | Press., psig | FeCl$_3$, %* | Chlorine, g/hr | Run time, hr |
| 1 | 250 | 350 | 16 | 18 | 15 |
| 2 | 250 | 350 | 16 | 24 | 7 |
| 3 | 250 | 350 | 16 | 23 | 18 |

TABLE 1-continued

| Run No. | Temp., °C. | Chlorination Conditions | | | |
|---|---|---|---|---|---|
| | | Press., psig | FeCl$_3$, %* | Chlorine, g/hr | Run time, hr |
| 4 | 300 | 550 | 16 | 37 | 6.5 |

*Amount calculated from analysis of the total iron in the system; it includes the tetrachloroferrate counter ion of all compounds of Formula I present. No ferric chloride was added.

TABLE 2

| Component | Init. conc., wt. % | Chlorination Results | | | |
|---|---|---|---|---|---|
| | | Final Concentration, wt. % | | | |
| | | Run 1 | Run 2 | Run 3 | Run 4 |
| Pentachloropyridine | 5.3 | 34.6 | 39.2 | 34.7 | 33.1 |
| Compound of Formula IA | 23.4 | 2.1 | 0.0 | 0.0 | 0.0 |
| trichloropyridines | 0.4 | 0.0 | 0.0 | 0.0 | 0.0 |
| tetrachloropyridines | 5.2 | 0.9 | 0.2 | 0.0 | 0.9 |
| monochloro(trichloromethyl)pyridines | 0.2 | 0.3 | 0.3 | 0.0 | 0.3 |
| dichloro(trichloromethyl)pyridines | 4.5 | 1.7 | 2.6 | 0.4 | 0.9 |
| trichloro(trichloromethyl)pyridines | 10.6 | 1.6 | 0.7 | 0.1 | 2.8 |
| tetrachloro(trichloromethyl)pyridines | 1.4 | 0.0 | 0.0 | 0.0 | 2.0 |
| Hexachlorobenzene | 1 | 1 | 1 | 1 | 1 |
| Ferric chloride | 16 | 16 | 16 | 16 | 16 |
| Low and non-volatile | 32 | 42 | 40 | 48 | 43 |

What is claimed is:

1. A process for preparing pentachloropyridine which comprises chlorinating a polychlorodipyridoimidazolium tetrachloroferrate compound of the formula

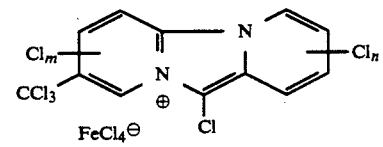

wherein
m represents the number 0 or 1; and
n represents the number 1, 2, 3, or 4
at a temperature of at least about 230° C. and a pressure of at least about 200 psig (1.48 mPa), optionally in the presence of a Lewis acid catalyst.

2. A process according to claim 1 wherein the Lewis acid catalyst ferric chloride is present.

3. A process according to claim 1 wherein the temperature is about 250° C.

4. A process according to claim 1 wherein the pressure is about 350 psig (2.52 mPa).

5. A process according to claim 1 wherein the polychlorodipyridoimidazolium tetrachloroferrate compound is the compound:

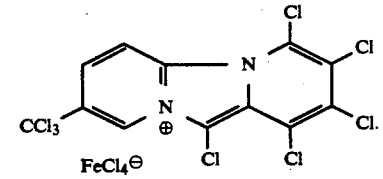

6. A process according to claim 1 wherein the polychlorodipyridoimidazolium tetrachloroferrate compound is obtained as a by-product from a process wherein a chloro(trichloromethyl)compound is chlorinated in the liquid phase in the presence of ferric chloride and is employed as a mixture with other by-products of that process.

* * * * *